United States Patent [19]
van der Maas et al.

[11] Patent Number: 5,478,378
[45] Date of Patent: Dec. 26, 1995

[54] FILTER WITH QUICK-CHANGE COUPLING FOR CLEANING GASES

[75] Inventors: Marinus F. van der Maas, Arnemuiden; Ewit de Kuyper, Cruquius, both of Netherlands

[73] Assignee: Scientific Glass Technology Exploitatie B.V., Middelburg, Netherlands

[21] Appl. No.: 180,959

[22] Filed: Jan. 13, 1994

[30] Foreign Application Priority Data

Jan. 15, 1993 [NL] Netherlands ............................ 9300082

[51] Int. Cl.$^6$ ................................................. G01N 30/60
[52] U.S. Cl. ................... 96/106; 55/274; 55/505
[58] Field of Search ........................... 96/106; 95/85, 95/88, 89; 210/198.2; 55/505, 274

[56] References Cited

U.S. PATENT DOCUMENTS

| | | | |
|---|---|---|---|
| 3,954,616 | 5/1976 | Hunt | 96/106 X |
| 4,116,836 | 9/1978 | de Angelis | 96/106 X |
| 4,131,547 | 12/1978 | Michel et al. | 96/106 X |
| 4,758,340 | 7/1988 | Marchand et al. | 96/106 X |
| 5,236,593 | 8/1993 | Cortes et al. | 96/106 X |
| 5,236,668 | 8/1993 | Higdon | 96/106 X |

FOREIGN PATENT DOCUMENTS

| | | |
|---|---|---|
| 0305875 | 3/1989 | European Pat. Off. . |
| 6513614 | 4/1966 | Netherlands . |
| 1335347 | 10/1973 | United Kingdom ..... 96/106 |
| 1399397 | 7/1975 | United Kingdom ..... 96/106 |

OTHER PUBLICATIONS

"Filters and Filtration Handbook", Christopher Dickenson, 1992, Elsevier, Oxford, Great Britain, pp. 555–556.
"Cromatographie in der Gasphase", r. Kaiser, 1965, Bibliographisches Institute Mannheim, Mannheim, pp. 80–83.

*Primary Examiner*—Richard L. Chiesa
*Attorney, Agent, or Firm*—Weingarten, Schurgin, Gagnebin & Hayes

[57] ABSTRACT

The invention relates to a filter for cleaning gases, provided with a quick-change coupling having an inlet and an outlet channel, and a hollow filter material housing filled with filter material through which, in operation, the gas to be cleaned flows. According to the invention, the filter material housing and the quick-change coupling are manufactured from materials that do not react with the gases to be cleaned and which do not release any substances during operation. The filter material housing may for instance be manufactured from glass and the quick-change coupling from stainless steel.

5 Claims, 1 Drawing Sheet

U.S. Patent
Dec. 26, 1995
5,478,378
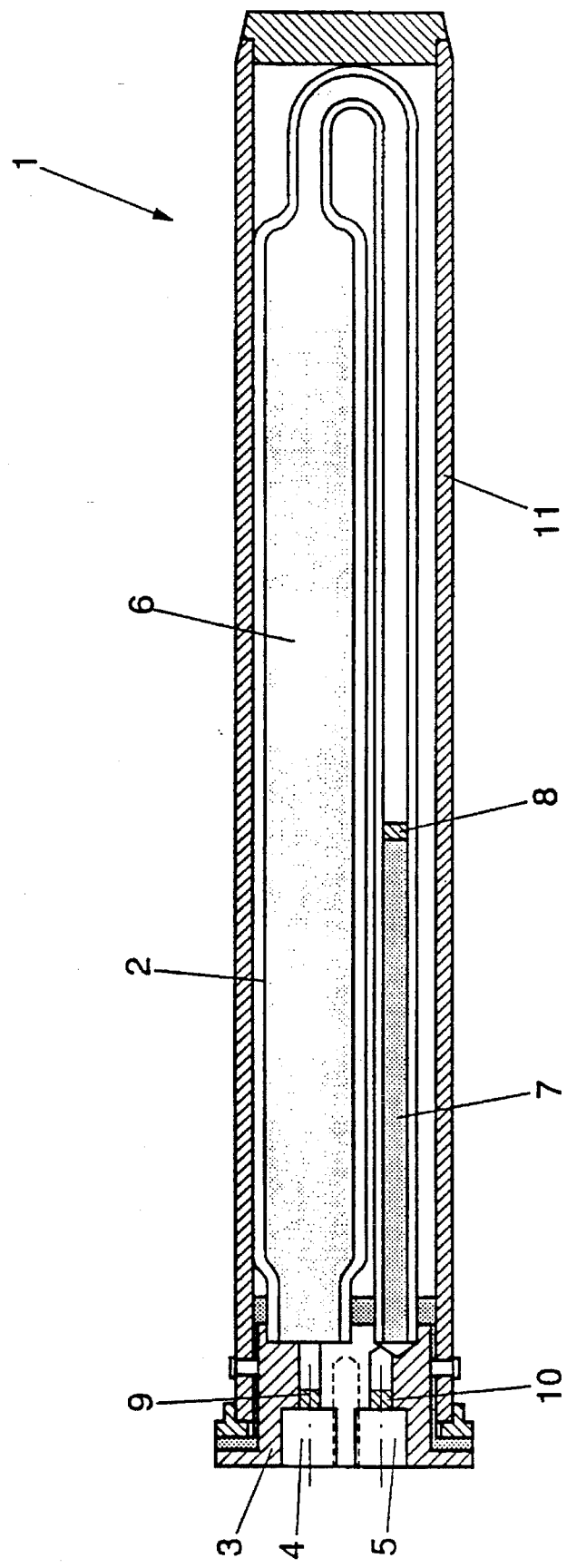

FILTER WITH QUICK-CHANGE COUPLING FOR CLEANING GASES

FIELD OF THE INVENTION

This invention relates to a filter for cleaning gases, comprising a quick-change coupling with an inlet and an outlet channel, and a hollow filter material housing filled with filter material through which, in operation, the gas to be cleaned flows.

BACKGROUND OF THE INVENTION

Such filters are used in processes requiring a very good cleaning of gases, for instance gases fed to a detection space of a measuring process, such as gas chromatography. These gases typically pass a plurality of filters of the above-mentioned type. The filters are for instance arranged in series and are connected to a line through which the gas to be cleaned flows. After a passage of time, the filter material is saturated to such an extent that it no longer has a filtering effect. This can be observed, for instance, by means of an indicator which may also be located in the filter material housing. When the filter material of one of the filters is saturated, the filter with the quick-change coupling can be removed from the gas line and replaced by a new filter. The gas-carrying line is provided with a number of coupling pieces to which the filters can be connected by means of the quick-change couplings. When a filter is connected to a coupling piece of the gas-carrying line, the gas flows out of the gas-carrying line via the filter and when no filter is connected to the coupling piece, the connecting openings of the coupling piece are closed hermetically, the gas flows on in the gas-carrying line and no gas is allowed to flow away from the line via the coupling piece or flow from the surroundings into the gas-carrying line. Hence, the quick-change couplings enable a normal continuation of the process for the purpose of which the gases are cleaned, even when a filter is being replaced.

The processes for the purpose of which the gases are cleaned, such as, for instance, detection processes, are becoming increasingly accurate, which necessitates an increasingly better cleaning of the gases. Detection processes with a detection limit of $10^{-14}$, i.e. a detection process in which one particle in $10^{-14}$ particles can be detected, are no longer an exception.

The known filter cannot be used for such highly accurate processes. This is caused by the fact that the known filters are manufactured from synthetic material, such as, for instance, acrylate or lexan. With the known filters, acrylate or lexan is chosen in view of the fact that this material is transparent, which is important for the perceptibility of the indicator and in view of the fact that synthetic material can be processed more easily and was moreover considered to exhibit good resistance to high pressures.

However, the drawback of the synthetic filter material housings and quick-change couplings is that the softeners and similar solvents are released from the synthetic material, particularly when the pressure in the gas-carrying line is low. The released softeners and the solvents disturb the processes for the purpose of which the gases are cleaned. Particularly in the case of accurate detection processes, with a detection limit of $10^{-14}$, for instance, detection becomes impossible.

SUMMARY OF THE INVENTION

The object of the invention is to provide a filter without the above-described drawback.

According to the invention, the filter of the type mentioned in the preamble is characterized in that the filter material housing and the quick-change coupling are manufactured from materials that do not react with the gases to be cleaned and do not release any substances during operation.

A filter of such design offers the advantage that it can be used in processes requiring a very pure cleaning of the gases to be fed in those processes, because the materials from which the filter is manufactured are completely inert to the gases to be cleaned, and, moreover, do not release any substances under the influence of a low pressure, for instance.

After a passage of time, the filter material becomes saturated and should then be cleaned. In the case of the known filters, manufactured from acrylate or lexan, regeneration of the filter material is carried out by companies especially equipped for this purpose. The filter material is removed from the filter material housing and is subsequently regenerated. This involves the loss of the quick-change coupling and the filter material housing of the known filter. Moreover, the known filters normally comprise an indicator which, as has already been described, indicates whether the filter material is saturated. These indicators usually contain heavy metals and other environmentally detrimental substances. With the disposal of the filter material housing, the indicator also ends up in the environment, which is fundamentally unacceptable.

According to a further elaboration of the invention, the filter housing and the quick-change coupling can be detachably connected with each other. A filter of such design offers the advantage that the filter can be removed and the filter material located in the filter material housing can be replaced by new filter material without involving the loss of the filter material housing and the quick-change coupling. Hence, the filter material housing and the quick-change coupling are suitable for reuse and need not be discarded, so that they do not form any burden to the environment.

According to a further elaboration of the invention, it is particularly favorable if at least the filter material housing is manufacured from heat-resistant material.

A filter of such design offers the advantage that the filter material need not be removed from the filter material housing for the purpose of the cleaning thereof. The filter material can be heated while located in the filter material housing, because the latter is heat-resistant. When during heating, for instance hydrogen gas is passed through the filter material, the filter material is cleaned and is suitable for reuse. Heating may take place externally, for instance by means of burners or radiant-heat elements. If so desired, cleaning may even take place without the filter being disconnected from the normal gas-carrying line. Obviously, this requires the presence of a bypass in the gas-carrying line to enable the process gas to be diverted and the line section carrying the coupling piece to be connected to a hydrogen gas source, for instance. Such a filter can be used several times and need not be discarded, so that the harmful substances of the indicator do not end up in the environment either. As it is not necessary to remove the filter for cleaning the filter material, the cleaning can be carried out at lower costs.

If the filter material housing is moreover resistant to very low temperatures, the filter material housing, in operation, can be suspended in a Dewar flask with, for instance, liquid nitrogen or a similar gas having a low condensation temperature. In principle, a filter cooled down to such a low temperature acquires the activity of a cryogenic pump, allowing the gases to be cleaned down to a molecular level. Obviously, this is not possible with the known filters, because under such circumstances, the acrylate or lexan becomes far too brittle and breaks.

According to the invention, the filter material housing can be manufactured from glass and the quick-change coupling from a metal such as, for instance, stainless steel or aluminum.

Glass meets all above-described properties and is moreover a relatively cheap material.

For the protection of the filter material housing, the filter according to the invention may be provided with a guard, which may or may not be detachably connected to the quick-change coupling and which encloses the filter material housing.

BRIEF DESCRIPTION OF THE DRAWING

In explanation of the invention, an exemplary embodiment of the filter will be described hereinafter with reference to the accompanying sole drawing FIGURE.

DETAILED DESCRIPTION OF THE PREFERRED INVENTION

The drawing shows a filter 1, comprising a filter material housing 2, a quick-change coupling 3. The filter material housing 2 is connected to the quick-change coupling 3. The quick-change coupling 3 comprises an inlet channel 4 and an outlet channel 5 connecting to the open ends of the filter material housing 2, designed as a glass pipe bent into a U-shape. The quick-change coupling 3 is manufactured from metal and preferably from stainless steel. This choice of material allows the filter to be used in the case of gases that have to be cleaned very thoroughly, for instance for the purpose of gas chromatography with a detection limit of $10^{-14}$. The filter material housing 2 is filled with filter material 6. Arranged in the vicinity of the open end of the filter material housing, which open end functions as outlet, is an indicator 7. Typically, this is a substance which colors upon saturation of the filter material 6. The indicator and the filter material are separated from each other by an element 8, permeable to gas. Such elements 9 and 10 are also arranged in the inlet and outlet channels 4 and 5 respectively of the quick-change coupling 3 so as to prevent the filter material 6 and/or the indicator substance 7 from finding its way into the gas-carrying line to which the filter 1 is connected. For the protection of the filter material housing 2, the filter is provided with a transparent guard 11, which may or may not be detachably connected to the quick-change coupling 3.

It is understood that the invention is not limited to the exemplary embodiment described, but that various modifications are possible within the scope of the invention.

We claim:

1. A filter for cleaning gases, comprising a quick-change coupling (3) having an inlet and an outlet channel (4 and 5 respectively), a hollow filter material housing (2) connected to the quick-change coupling and filled with filter material (6) through which, in operation, the gas to be cleaned flows via the inlet and outlet channels, and a transparent guard (11) enclosing the filter material housing, wherein the filter material housing (2) and the quick-change coupling (3) each comprise a material that does not react with the gases to be cleaned and does not release any substances during operation, the filter material housing (2) comprising a heat-resistant glass and the quick-change coupling (3) comprising stainless steel or aluminum.

2. A filter according to claim 1, wherein the filter material housing (2) and the quick-change coupling (3) are detachably connected to each other.

3. A filter according to claim 1, wherein at least the filter material housing (2) comprises a material resistant to very low temperatures.

4. A filter according to claim 1, wherein the guard (11) may or may not be detachably connected to the quick-change coupling (3).

5. A filter according to claim 1, wherein said guard is detachably connected to the quick-change coupling (3).

* * * * *

UNITED STATES PATENT AND TRADEMARK OFFICE
CERTIFICATE OF CORRECTION

PATENT NO. : 5,478,378
DATED : December 26, 1995
INVENTOR(S) : Marinus F. van der Maas; et al It is certified that error appears in the above-indentified patent and that said Letters Patent is hereby corrected as shown below:

Column 1, line 44, delete "$10^{-14}$" and insert --$10^{14}$--.

Signed and Sealed this

Thirteenth Day of May, 1997

Attest:

BRUCE LEHMAN

Attesting Officer      Commissioner of Patents and Trademarks